US009157156B2

(12) United States Patent
Anelli et al.

(10) Patent No.: US 9,157,156 B2
(45) Date of Patent: Oct. 13, 2015

(54) PROCESS FOR THE PREPARATION OF A IODINATING AGENT

(75) Inventors: Pier Lucio Anelli, Milan (IT); Carlo Felice Viscardi, Milan (IT); Pietro Delogu, Torviscosa (IT); Fabrizio Goffredi, Torviscosa (IT); Alfonso Nardelli, Torviscosa (IT); Giovanni Battista Giovenzana, Novara (IT)

(73) Assignee: Bracco Imaging S.P.A., Milan (IT)

( * ) Notice: Subject to any disclaimer, the term of this patent is extended or adjusted under 35 U.S.C. 154(b) by 0 days.

(21) Appl. No.: 13/375,797

(22) PCT Filed: Jul. 6, 2010

(86) PCT No.: PCT/EP2010/059619

§ 371 (c)(1),
(2), (4) Date: Dec. 2, 2011

(87) PCT Pub. No.: WO2011/003894

PCT Pub. Date: Jan. 13, 2011

(65) Prior Publication Data

US 2012/0088926 A1   Apr. 12, 2012

(30) Foreign Application Priority Data

Jul. 7, 2009   (IT) .............................. MI2009A1201

(51) Int. Cl.
*C07C 69/34* (2006.01)
*C25B 1/24* (2006.01)
*C07C 227/16* (2006.01)
*C07C 231/12* (2006.01)

(52) U.S. Cl.
CPC ................. *C25B 1/24* (2013.01); *C07C 227/16* (2013.01); *C07C 231/12* (2013.01)

(58) Field of Classification Search
CPC ....................................................... C07C 69/34
USPC ....................................................... 560/193
See application file for complete search history.

(56) References Cited

U.S. PATENT DOCUMENTS

| 3,647,864 | A | 3/1972 | Ackerman |
| 3,833,490 | A | 9/1974 | Bizot et al. |
| 5,013,865 | A | 5/1991 | Cross et al. |
| 5,575,905 | A | 11/1996 | Wistrand et al. |
| 5,728,877 | A | 3/1998 | Anelli et al. |
| 5,763,650 | A * | 6/1998 | Mauro et al. ................. 562/456 |
| 5,763,663 | A | 6/1998 | Anelli et al. |
| 6,420,603 | B1 | 7/2002 | Alessandroni et al. |
| 8,383,868 | B2 | 2/2013 | Yoshida et al. |
| 8,648,223 | B2 | 2/2014 | Yoshida et al. |
| 8,809,602 | B2 | 8/2014 | Yoshida et al. |
| 2008/0146853 | A1 | 6/2008 | Midorikawa et al. |
| 2010/0331567 | A1 | 12/2010 | Giovenzana et al. |

FOREIGN PATENT DOCUMENTS

| CA | 2002599 A1 | 5/1990 |
| CA | 2020489 A1 | 11/2005 |
| CN | 1328539 A | 12/2001 |
| DE | 124516 A1 | 3/1977 |
| DE | 68912920 T2 | 8/1994 |
| EP | 0083964 A1 | 7/1983 |
| EP | 0365541 A1 | 5/1990 |
| EP | 0376858 A2 | 7/1990 |
| EP | 0773923 A1 | 5/1997 |
| EP | 0782562 A1 | 7/1997 |
| EP | 0828705 A1 | 3/1998 |
| GB | 1548594 A | 7/1979 |
| GB | 1472050 A | 4/1997 |
| JP | H01-141803 A | 6/1989 |
| JP | H01-160804 A | 6/1989 |
| JP | 10-506653 A | 6/1998 |
| JP | 11-505827 A | 5/1999 |
| JP | 2000264605 A | 9/2000 |
| RU | 2060246 C1 | 5/1996 |
| RU | 2278816 C2 | 6/2006 |
| WO | 88-09328 A1 | 12/1988 |
| WO | 92-14695 A1 | 9/1992 |
| WO | 94-14478 A1 | 7/1994 |
| WO | 96-37458 A1 | 11/1996 |
| WO | 96-37461 A1 | 11/1996 |
| WO | 97/05097 A | 2/1997 |
| WO | 98-28259 A1 | 7/1998 |
| WO | 00/32561 A | 6/2000 |
| WO | 2008-111521 A1 | 9/2008 |

OTHER PUBLICATIONS

PCT International Search Report for PCT/EP2010/059619, mail date Oct. 7, 2010.
PCT Written Opinion of the International Searching Authority for PCT/EP2010/059619, mail date Oct. 7, 2010.
Lines, Robert et al., "Electrophilic Aromatic Substitution by ositive loding Species. Iodination of Deactivated Aromatic Compounds", Acta Chemica Scandinavica, Series B: Organic Chemistry and Biochemistry, Munksgaard, Copenhagen, DK, vol. B34, Jan. 1, 1980, pp. 47-51, XP002491791, ISSN: 0302-4369.
PCT International Search Report for PCT/EP2009/051747, mail date Nov. 4, 2009.
PCT Written Opinion of the International Searching Authority for PCT/EP2009/051747, mail date Nov. 4, 2009.
Miller, Larry L. et al., "Scope and Mechanism of Aromatic Iodination with Electrochemically Generated Iodine (I)", Journal of the American Chemical Society, vol. 98, No. 6, Mar. 17, 1976, pp. 1515-1519, XP002491790, Colorado State University, Fort Collins, Colorado.
Third Party Observation for European application No. 09713167.6, mail date Apr. 3, 2012.

(Continued)

*Primary Examiner* — Yong Chu
*Assistant Examiner* — Sonya Wright
(74) *Attorney, Agent, or Firm* — VIVICAR Law, PLLC (57) ABSTRACT

The present invention describes a process for the synthesis of a iodinating agent, being said iodinating agent iodine chloride (ICl.) In particular, the present invention relates to a process for the electrochemical preparation of ICl, as a useful iodinating agent in the preparation of iodinated organic compounds for use as contrast agents or their precursors in the synthesis of the same.

17 Claims, 3 Drawing Sheets

(56) References Cited

OTHER PUBLICATIONS

First Office Action for Chinese application No. 201080027573.3, mail date Nov. 12, 2013 (English translation).
Alemi, Abdolali et al., "The Novel Route for Synthesis of Tellurium Tetrachloride, and Redetermination of Its Structure At Lower Temperature by X-Ray Crystallography", Acta Chim. Slov., vol. 47, 2000, pp. 89-98.
Greene, Theodora W., "Protective Groups in Organic Synthesis", John Wiley & Sons, 1981, Chapter 2: Protection for the Hydroxyl Group Including 1,2- and 1,3-Diols.
Soled, Stuart et al., Acta Cryst., "The Crystal Structures of $KICl_2$ and $KICl_2,H_2O$", 1973, B29, pp. 2104-2109.
The Merck Idex, 13th Edition, Merck & Co., Inc., Whitehouse Station, New Jersey, 2001, item Nos. 5071 and 5073, p. 908-909, ISBN No. 0911910-13-1.
Zittel, H.E. et al., "A Glassy-Carbon Electrode for Voltammetry", Analytical Chemistry, vol. 37, No. 2, 1965, pp. 200-203.
Office Action for Canadian application No. 2,715,430, mail date Jul. 3, 2014.
Office Action for Canadian application No. 2,763,405, mail date Jul. 24, 2012.
Final Office Action for Japanese application No. 2010-547157, mail date Feb. 4, 2014 (English translation).
Office Action for Japanese application No. 2012-518962, mail date May 7, 2014 (English translation).
Office Action for Mexican application No. MX/a/2010/009184, mail date Mar. 10, 2014 (English translation).
Decision on Grant for Russian application No. 2012103998, mail date May 5, 2014 (English translation).
Office Action for Canadian application No. 2,715,430, mail date Apr. 23, 2015.
Office Action for Indian application No. 5769/CHENP/2010, mail date Feb. 26, 2015.
Office Action—First for New Zealand application No. 596447, mail date Oct. 1, 2012.
Office Action—Second for New Zealand application No. 596447, mail date Oct. 18, 2013.
Office Action for Israeli application No. 207640, mail date Mar. 12, 2015 (English translation).
Office Action for European application No. EP09713167.6, mail date May 11, 2015.
Office Action for Mexican application No. MX/a/2010/009184, mail date Dec. 19, 2014 (English translation).
Office Action: Notice of Allowance for U.S. Appl. No. 12/918,001, mail date Feb. 27, 2015.
First Office Action for Australian application No. 2009216783, mail date Apr. 13, 2012.
First Office Action for Australian application No. 2010270302, mail date Jun. 28, 2013.
First Office Action for Chinese application No. 200980105904.8, mail date Sep. 5, 2012 (English translation).
Office Action for European application No. 09713167.6, mail date Sep. 16, 2011.
Office Action for European application No. 09713167.6, mail date Mar. 20, 2013.
Office Action for Japanese application No. 2010-547157, mail date Mar. 12, 2013 (English translation).
Office Action for New Zealand application No. 586944, mail date Oct. 20, 2011.
Decision on Grant of Patent for Invention for Russian application No. 2010138570, mail date Jul. 31, 2012 (English translation).
Search Report and Written Opinion for Singaporean application No. 201108724-4, mail date Aug. 10, 2012.
Office Action for Korean application No. 10-2010-7017162, mail date Jun. 1, 2015 (English translation) [B0619].

\* cited by examiner

PROCESS FOR THE PREPARATION OF A IODINATING AGENT

CROSS-REFERENCE TO RELATED APPLICATIONS

This application is the national stage application of corresponding international application number PCT/EP2010/059619 filed Jul. 6, 2010, which claims priority to and the benefit of Italian application no. MI2009A001201, filed Jul. 7, 2009, all of which are hereby incorporated by reference.

The present invention generally relates to a process for the preparation of a iodinating agent. More specifically, this invention relates to a process for the electrochemical preparation of iodine chloride (ICl), useful iodinating agent in the synthesis of iodinated organic compounds, such as 2,4,6-triiodophenyl derivatives, employable as contrast agents or as precursors in the synthesis of the same.

BACKGROUND

Contrast media (or contrast agents) and their use in the diagnostic filed are widely described in literature.

In particular, iodinated aromatic derivatives are among the classes of compounds that find an application as contrast agents in diagnostic techniques which relying on the absorption of X rays by the tissues or organs (i.e. radiography, tomography). Among these aromatic iodinated derivatives it is worth mention, inter alia, Iohexol (GB 1,548,594—Nyegaard & Co. A/S) Ioversol (EP 83964—Mallinckrodt Inc.), Iopamidol (GB 1,472,050—Bracco) and Iomeprol (EP 365541—Bracco). These iodinated contrast agents are prepared by various synthetic routes described in literature, whereby some of such synthetic route comprise the poly-iodination of an aromatic intermediate, in particular a phenol or aniline derivative intermediate, by means of different iodinating agents. More specifically, EP773923 (Bracco) describes the iodination of 5-amino-1,3-benzenedicarboxylic acid with iodine chloride (ICl) in the presence of hydrochloric acid, to give the corresponding tri-iodine derivative according to the following scheme:

A substantially similar approach was also described for the iodination of 5-hydroxy-1,3-benzenedicarboxylic acid as reported, for example, in EP 782562 (Bracco). ICl can be prepared by methods known to the expert in the field, some of which contemplate the formation of a chlorinated species of I (III), typically $ICl_3$, and the subsequent conversion of the thus obtained intermediate, by the addition of molecular $I_2$, as schematically set forth below:

Among the possible methods to generate $ICl_3$ it may be mentioned, for instance, the use of $KClO_3$ by reaction with $I_2$ in the presence of hydrochloric acid (Acta Chim. Slovo. 2000, 47, 89-90) or the preparation according to JP 1141803 (Mitsui Toatsu Chemicals) that requires the use of gaseous chlorine as initial reagent:

Although this latter route enables the production of ICl with a high degree of purity, the use of gaseous chlorine, especially in an application on an industrial scale, involves the need of strict precautions and safety arrangements because of the toxicity and hazard of that gas.

Advantageously, we have now found a process for the preparation of ICl in high yields and high purity, which does not require the use of gaseous chlorine, avoiding thereby the above mentioned drawbacks typically associated with the use of large volumes of chlorine.

SUMMARY OF THE INVENTION

It is a first aspect of the present invention a process comprising the steps of:
a. electrochemically oxidizing 1 mole of starting ICl in acidic aqueous solution to give an intermediate derivative with an oxidation state of iodine equal to (III),
b. reacting said intermediate derivative with iodine, and
c. obtaining 3 moles of ICl.

The electrochemical oxidation is carried out in an electrolytic cell wherein the anodic and cathodic compartments are separated by an ion permeable separator. Preferred separator is a membrane permeable either to anions or cathions, where the preferred anionic membranes are made of a polymeric core such as polyamide, polyester, polystyrene, polyvinyl benzene and the like. Preferred cationic membranes are, e.g. polimeric fluorocarbonic membranes such as polytetrafluoroethylene (PTFE), tetrafluoro ethylene-perfluoropropylene copolymers (FEP), tetrafluoroethylene-perfluoroalkoxy copolymers (PFA), ethylene-tetrafluoroethylene copolymers (ETFE) and polyvinylidene fluoride (PVDF) and the like.

The electrode at the cathodic compartment is selected from those commonly known in the art, typically, a graphite electrode, whereas the anodic compartment is preferably made of: platinum, graphite or, more preferably, modified graphite or even more preferably, glassy carbon or vetrous carbon.

In a preferred embodiment of the invention, the process is carried out by means of an electrolytic cell wherein the anodic and the cathodic compartment are both made of the same material, such as graphite or modified graphite or glassy carbon.

At the anode, the solution comprises a starting amount of ICl, usually present as hydrochloric solution, in concentrations comprised from about 5% to about 50%, preferably from about 18 to about 36%.

At the cathode, the solution comprises water or a linear or branched ($C_1$-$C_4$) alcohol in a mixture with a strong inorganic acid, the concentration of the inorganic acid ranging from 5% to 50% by weight respect to the sum of the acid and water. Particularly preferred are concentrations ranging from 10% to 45%. Preferred inorganic acids are hydrochloride acid and sulphuric acid, whereas the cathode solution comprising water and hydrochloric acid is preferred, particularly with a concentration of hydrochloric acid ranging from about 5% to about 40% by weight. As said above, according to the present invention, the anodic oxidation of a starting mole of ICl leads prevalently to the formation in solution of an intermediate derivative wherein the formal oxidation state of the Iodine is (III), and the subsequent reaction with molecular Iodine allows the preparation of 3 moles of ICl. Said subsequent reaction with molecular iodine, may be performed by adding the solid iodine to the intermediate solution, being this latter transferred into a second reactor or left in the same reactor.

Preferably, the solution containing the Iodine in the formal oxidation state (III), is transferred into a separate reactor before carrying out the addition of molecular iodine.

According to a further embodiment, the present invention also refers to a process for the preparation of ICl by electrochemical oxidation of a solution containing a starting amount of the same, wherein an aliquot of the produced ICl is re-introduced as a starting reagent into the anodic compartment.

Furthermore, and according to a further object, the present invention discloses a process comprising the steps of:
a. electrochemical oxidation of 1 mole of ICl in acidic aqueous solution to give an intermediate derivative wherein the oxidation state of the iodine is (III),
b. reaction of the I(III) intermediate derivative obtained in step a with molecular iodine.
c. obtaining 3 moles of ICl; and
d. further iodinating a compound of formula (I)

I wherein:
R is —N(R')$_2$ or —OH;
R1 is independently in each occurrence —COOR', —CON(R')$_2$; and
R' is independently in each occurrence hydrogen or (C$_1$-C$_4$) linear or branched alkyl optionally substituted by one or more hydroxy groups present as such or in a protected form, to give a compound of formula (II)

II

In an alternative embodiment, the present invention also refers to a process wherein a part of the produced ICl is re-introduced as a starting reagent in the anodic compartment and part of the ICl is used as iodinating agent.

DETAILED DESCRIPTION OF THE INVENTION

Figure 1:
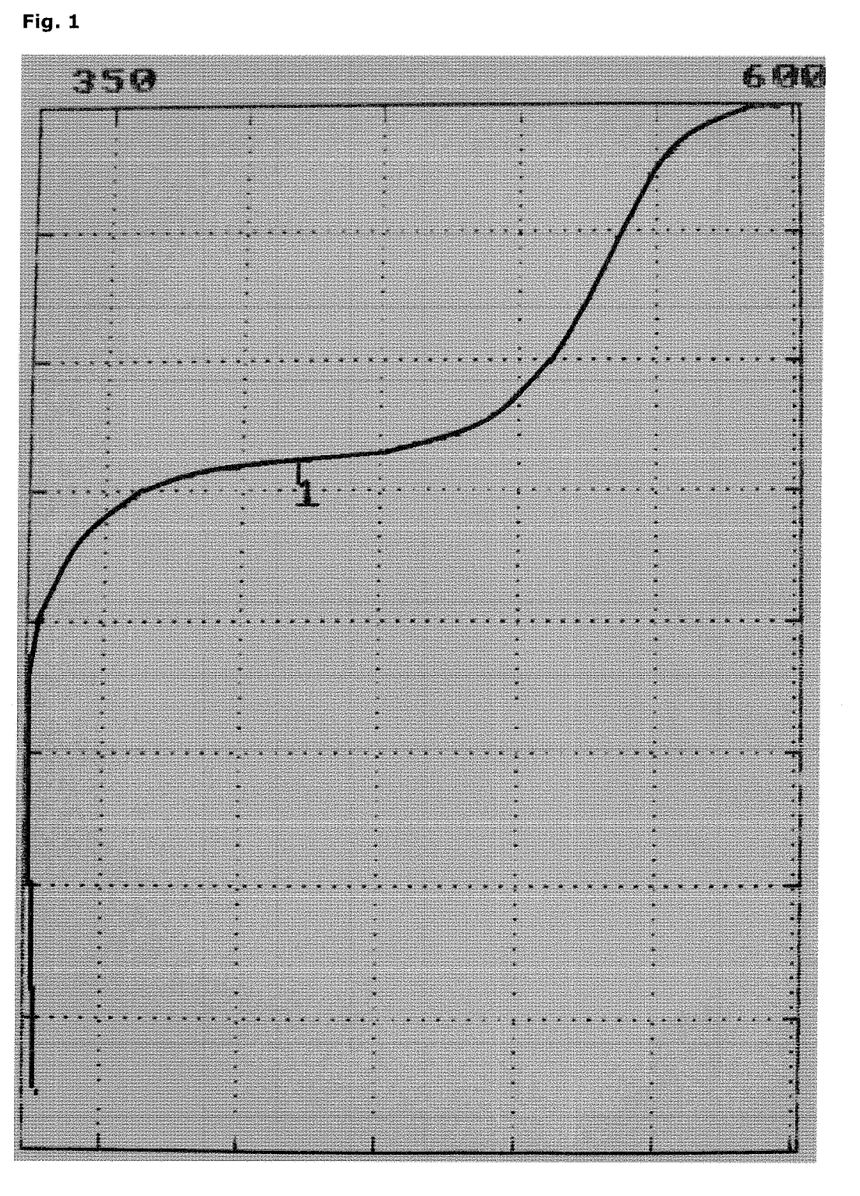
FIG. 1 shows a titration curve of the solution loaded in the anodic compartment of the electrochemical cell. The x-axis represents the values of the potential expressed in mVolt; the y-axis represents the amount of the KI (mL) added during the titration (see Example 1 before the starting of the reaction).
Figure 2:
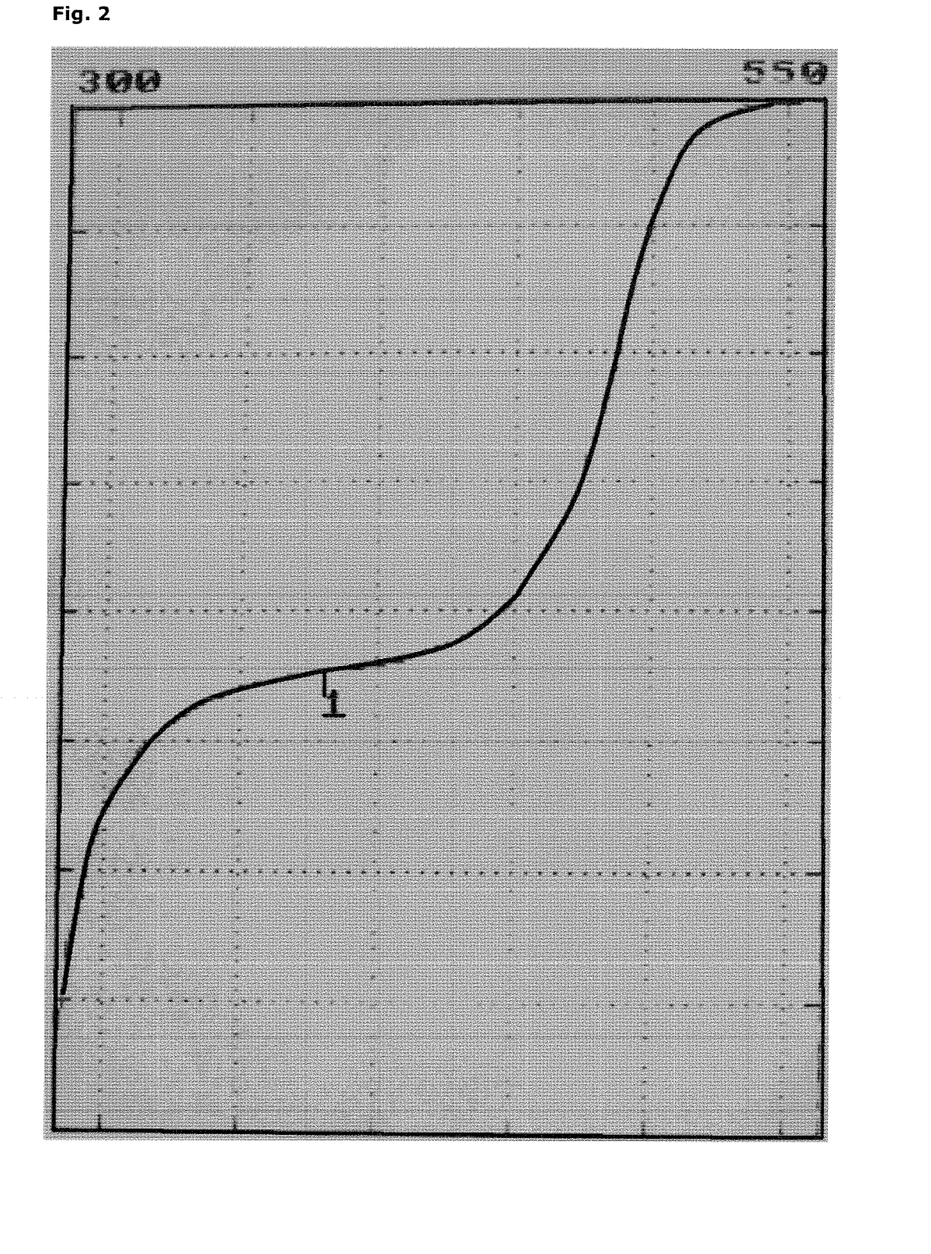
FIG. 2 shows a titration curve of the oxidised solution in the anodic compartment of the electrochemical cell. The x-axis represents the values of the potential expressed in mVolt; the y-axis represents the amount of the KI (mL) added during the titration (see Example 1 at the end of the reaction).
Figure 3:
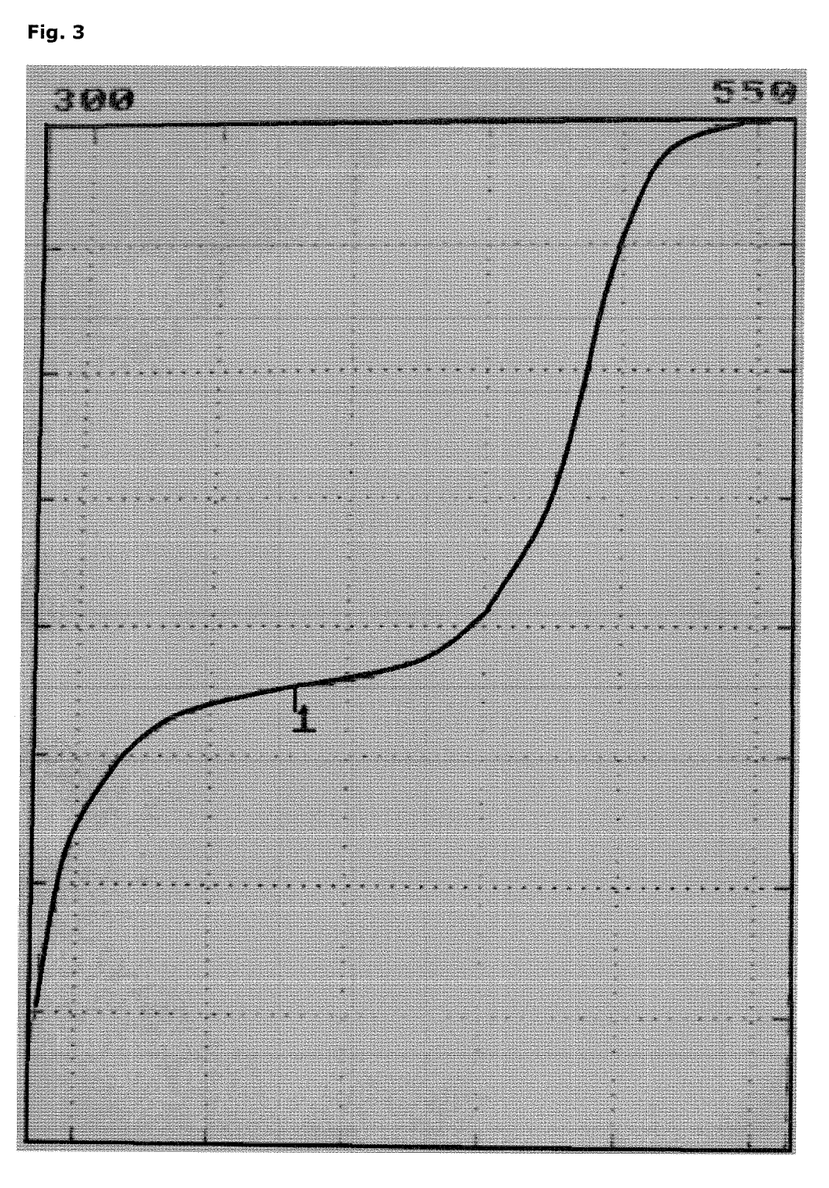
FIG. 3 shows a titration curve of the solution obtained after dissolution of I$_2$ in the electrochemically oxidized solution and the decantation of the iodine in excess. The x-axis represents the values of the potential expressed in mVolt; the y-axis represents the amount of the KI (mL) added during the titration (see Example 3 at the end of reaction).

The present invention generally relates to a process for the preparation of ICl by reaction of an appropriate derivative in which the formal oxidation state of the Iodine is (III), and hereinafter defined as "I(III)-derivative", with molecular iodine, wherein the I(III)-derivative is obtained by electrochemical oxidation of a starting amount of ICl in aqueous acidic solution. The intermediate I(III)-derivative is for example an interhalogen iodine-chlorine compound such as ICl$_3$, ICl$_4^-$ or similar, or even any possible mixture thereof.

To better illustrate the invention, it is herein reported the stoichiometry of the reaction and a general synthetic scheme (1) comprising the step-a, i.e. the anodic oxidation of a starting amount of ICl to give the intermediate I(III)-derivative (hereinafter generally indicated as ICl$_3$), followed by the reaction with solid iodine, according to step-b.:

(1)

Of note, and as evident from the stoichiometry of the synthetic scheme (1) above, the process of the invention advantageously allows to obtain 3 moles of ICl from a single initial mole of the same, substantially without the addition of gaseous chlorine.

As said above, the initial step-a of the present process comprises the anodic oxidation of ICl in an electrolytic cell. In this latter, the anode and the cathode compartments are conveniently separated by a suitable separator selected from those known in the art, e.g. diaphragms, porous or semi-permeable membranes or the like. The separator should be resistant to acid conditions, and it should be permeable to ionic species, and preferably permeable either to anions or cations, for instance only to anions, such as chloride. To this extent, the preferred membrane is made with a polymeric core such as polyamide, polyester, polystyrene, polyvinyl benzene and the like. Many of these membranes are commercially available, such as, among others, the Neosepta® AHA, the Selemion® AMV, the FUMASEP® or IONAC MA®.

Also preferred are those membranes constituted of a polimeric fluorocarbonic core such as Nafion® PSFA N115 membrane (available from Du Pont SpA) or Selemion® HSF and Selemion® CMF (available from Asahi Glass Co).

Other preferred separator is a membrane that is selective to the passage of ions in terms of steric hindrance, which is to be intended in terms of ionic size.

Preferably, the electrochemical oxidation is carried out in an electrolytic cell in which the two compartments anode/cathode are separated by a Fumasep FTAM-E® type membrane.

Examples of possible electrodes employable in the present process are those conventionally adopted in industrial applications.

At the cathode compartment the electrode is, for example, made of graphite, palladium, lead, copper or steel, or mixtures thereof, whereas the electrode made of graphite is particularly preferred.

At the anode portion, the electrode is made of a metal selected from those typically used in similar electrochemical systems, e.g. platinum or other elements of the Group VIII of the periodic table, preferably in a reticular form. Furthermore, the electrode at the anode is also made by materials suitably coated with metals which are resistant to corrosion, for example coated with a film of suitable thickness of metals typically chosen in the eighth group of the periodic table (platinum, rhodium, ruthenium, iridium) or mixtures thereof.

Embodiments wherein the anode is made of non-metallic conductive materials employable as electrodes such as graphite, conductive ceramics or glassy (or vetrous) carbon are also within the scope of the present invention, whereas the anode made of graphite is preferred.

Alternatively, the electrode at the anode is made of "modified graphite", which means a graphite suitably processed or treated so that its performance and duration under strong acidic conditions is enhanced. According to the present invention, examples of said modified graphite are polymeric matrix coated or impregnated graphites, or specially produced graphites.

In this respect, suitable polymeric matrixes are for example methacrylic resins, phenolyc resins or the like. Thus, and according to a further preferred embodiment, the electrode at the anode is made of a polymeric matrix impregnated graphite. Equally preferred is a polymeric matrix constituted of a methacrylic resin or a phenolyc resin.

Likewise, and it is a still more preferred embodiment, the electrode at the anode is made of glassy (or vetrous) carbon, a material showing a combination of glassy and ceramic properties with those of graphite (for a general reference see: Analytical Chemistry; Vol 37, No2, 1965, pag 200-202).

According to an embodiment of the invention, the cathode and the anode are made of different materials, and more preferably, the electrolytic cell comprises a cathode made of graphite and an anode made of platinum, even more preferably, this latter being in the form of a grid.

Alternatively, and this is an equally preferred embodiment of the invention, both cathode and anode are made of the same material selected from: graphite, modified graphite, or glassy carbon.

As previously mentioned, the electro-chemical reaction for the generation of the I(III)-derivative according to the present invention is carried out in a suitable solvent and operating in acidic conditions, preferably at pH below 4, more preferably at pH below 2 or even more preferably at pH below 1.

Typically, said operative conditions are obtained by operating in the presence of a strong inorganic acid at the cathode, such as hydrochloric acid or sulfuric acid, in a solvent system comprising water, ($C_1$-$C_4$) lower alcohols, or mixtures thereof, with a concentration of the inorganic acid ranging from 5% to 50% by weight respect to the sum of the acid and solvent. Particularly preferred are concentrations ranging from about 10% to about 45%.

The term "($C_1$-$C_4$) lower alcohols" means any linear or branched alcohols with 1 to 4 carbon atoms such as methanol, ethanol, propanol, butanol and the like. More preferably, the electrochemical reaction at the cathode is conducted in the presence of hydrochloric acid and water with the concentration of hydrochloric acid ranging from 5% to 40% by weight.

According to a fundamental principle of the electrochemistry it will be recognized that if at the anode the electrochemical oxidation, with the formation of I(III)-derivative from ICl, occurs, at the cathode the corresponding reduction will be observed; in detail, in this case, the formation of hydrogen ($H_2$) by reduction of the $H^+$ ions will occur. The gaseous hydrogen ($H_2$) thus produced can then be recovered by methods conventionally used in electrochemical industrial process, for instance by means of recovery membranes and the like.

Therefore, and as detailed in the experimental part, the cathode compartment will be properly loaded with the aqueous acidic solution of choice, such as a solution of water and hydrochloric acid with a concentration of hydrochloric acid ranging from 5% to 50% by weight, whilst in the anodic compartment, an initial amount of ICl will be appropriately loaded, usually present as a hydrochloric solution, in a concentration from about 5% to about 50% by weight, preferably from 15% to 40% by weight.

The electrochemical cell of the process of the invention generally works in galvanostatic or potentiostatic mode. Preferred mode is the galvanostatic mode, operating at values of current density comprised from about 50 to 500 mA/cm$^{-2}$, preferably from about 50 to about 150 mA/cm$^{-2}$. Accordingly, the potential values will be such as to maintain that current densities in the electrochemical cells for sufficient time to reach the desired degree of oxidation of the anodic solution. Desired degree of oxidation are those greater than 80%, preferably grater than 90%, achievable with a reaction time that may vary from several hours (more than 40 hrs) to days (even 2 or more days) depending on the ratio between the batch size and the electrode surface. The course of the reaction can be monitored by appropriate conventional analytical methods, including, for example, the detection of the variation of the potential by means of platinum combined electrodes, using Ag/AgCl electrode as the standard reference.

As previously indicated, the present process involves the formation of an intermediate I(III)-derivative that is further processed for the production of 3 moles of ICl by reaction with molecular iodine. The detection of the formation of said intermediate is carried out by conventional methods known in the art, including, for instance, titration of the anodic solution at the end the electrolysis by using potassium iodide (KI) in an acid environment or similar.

In more detail and according to a preferred embodiment of the invention, the anodic solution is reacted with solid iodine (preferably in a slight molar excess) in a second reactor or alternatively "in situ" (which means in the same reactor). The reaction, conducted at room temperature and under stirring, leads to the formation of ICl in solution in high yield (almost quantitative), along with a residue of solid iodine that is removed by decantation, filtration or centrifugation.

A practical preferred embodiment of the process of the invention is carried out as follows: in an electrochemical cell comprising a cathodic and an anodic compartment, separated by a suitable ion permeable membrane, an aqueous solution of HCl is loaded as cathodic reagent, and a starting solution of iodine chloride, HCl and water as anodic reagent. The cell is fed with a DC electric current operating at a current density of about 100 mA/cm$^{-2}$ or at a selected current voltage according to the adopted operative mode. At the end of the electrolytic process, the anodic solution is titrated for the speciation of the iodine compounds thus present. In line with what set forth above, the formal oxidation state resulting for at least part of the iodine present is (III). The solution containing iodine in the formal oxidation state (III) thus produced is hence transferred to a second reactor and added with an appropriate amount of solid iodine, operating at room temperature (i.e. 15° C.-30° C.) and under stirring. The solid residue is separated from the solution by decantation and during the dissolution of solid iodine the potential of anodic solution is monitored with a combined electrode, as previously indicated. The oxidation state of substantially all the iodine present in solution is (I).

The iodine chloride in hydrochloric solution thus obtained or, as specified below, part of it in case where a portion thereof is going to be recycled in the initial electrochemical cell, can be advantageously used for the iodination of organic molecules, e.g. for the poly-iodination of aromatic substrates.

According to a particularly advantageous embodiment, and taking into account the stoichiometry of the reaction that characterizes the entire process, said initial source of ICl can be constituted by a part of the ICl obtained as the product. By that, depending on the case, appropriate amount of the aqueous acid solution of ICl obtained as the product can be recycled and loaded at the anode compartment.

It is therefore a further aspect of the present invention, an electrochemical process for the preparation of ICl, substantially as formerly described, whereby an appropriate part of the produced ICl is re-introduced as a starting reagent in the anodic compartment. Clearly, in order to prevent the depletion or oversaturation of the anolitic source, for example, after some process cycles and ICl recycling, integrations with water, or with the acid of choice, such as hydrochloric acid, or even with aliquots of starting ICl itself, may be appropriate.

The iodine chloride, herein intended as starting compound of the present process, is generally used as a hydrochloric solution, as described in literature.

As previously mentioned, the ICl obtained according to the present process, may be conventionally used as a iodinating agent, especially in the poly-iodination of aromatic substrates for the preparation of non-ionic iodinated contrast media.

In this respect, it is a further object of this invention, a process comprising the steps of:

a. electrochemical oxidation of 1 mole of ICl in acidic aqueous solution to give an intermediate derivative wherein the oxidation state of the iodine is (III),
b. reaction of the I(III) intermediate derivative obtained in step a with molecular iodine,
c. obtaining 3 moles of ICl; and
d. further iodinating a compound of formula (I)

wherein:

R is —N(R')$_2$ or —OH;

R1 is independently in each occurrence —COOR', —CON(R')$_2$; and

R' is independently in each occurrence hydrogen or (C$_1$-C$_4$) linear or branched alkyl optionally substituted by one or more hydroxy groups present as such or in a protected form, to give a compound of formula (II)

Preferably, the process is performed starting from the compounds of formula I wherein R is a hydroxy (—OH) or amino group (—NH$_2$) and the groups R1 are the same and are chosen from —COOH or —CONHR'; wherein R' is chosen from —CH(CH$_2$OH)$_2$ or —CH$_2$(CHOH)CH$_2$OH.

In more detail, it is a further aspect of the invention a process comprising the preparation of the ICl as extensively set forth above, followed by its subsequent addition as iodinating agent to an aqueous solution of compound (I), the latter generally present in a slight excess, under stirring and a temperature of about 80-90° C. The pH is set to values comprised from 0 to about 2, optionally in the presence of a proper basic buffer (see for instance U.S. Pat. No. 5,013,865). The crude reaction mixture thus obtained may be hence processed by means of known techniques, such as filtration or chromatographic purification, leading to the desired tri-iodinated derivative in a pure form.

According to the alternative embodiment described above, the process provides for re-introducing a part of the produced ICl as a starting reagent in the anodic compartment, whilst part of the ICl is used as iodinating agent as described above. The hydroxyl groups in the class of compounds of formula I may be present as unprotected or alternatively, to avoid undesirable side reactions, as suitably protected by means of conventional methods and protecting groups known in the art (see for a general reference: T. W. Green, Protective Groups in Organic Synthesis (Wiley, N.Y. 1981)).

The substrates of formula I and the corresponding iodination reaction with ICl to give the corresponding compounds of formula II are well known in the art and widely described in literature, for instance for the preparation of Iopamidol or Iomeprol as already cited.

The following examples are provided in order to better illustrate the present invention, without in any way limiting the scope.

EXPERIMENTAL PART

Example 1

Electrochemical Oxidation of ICl in the Presence of a Platinum Anode

In an electrochemical cell comprising a cathodic compartment containing as the cathode a cylindrical rod of graphite having a surface area of 6 cm$^2$, and an anodic compartment containing as the anode a grid of platinum having a geometric surface area of 24 cm$^2$, where the two compartments are separated by a Fumasep® FTAM-E type anionic conduction membrane, 69.7 g of a solution of HCl 33% in water as cathodic reagent, and 134.7 g of a solution of iodine chloride having the following composition as anodic reagent:

ICl 30.8%
HCl 22.8%
H$_2$O 46.4%
were loaded.

The cell was fed with a continuous current of 610 mA for 21 h under a voltage of about 6.5 volts.

During the electrolysis the potential of the anodic solution was detected by a Pt combined electrode (reference Ag/AgCl). The starting potential of the solution before electrolysis was found to be 691 mV, whilst at the end of the electrolysis the potential was increased to 975 mV.

At the end of the electrolysis reaction, the anode solution was titrated with KI in acidic conditions for the speciation of the iodine derivatives. 1.73 mEq/g of solution of KI were consumed to obtain a point of inflection at a potential of 780 mV, compared to Pt combined electrode, and then 5.30 mEq/g of solution of KI were consumed to obtain a second point of inflection at a potential of 493 mV.

Accordingly, it was confirmed that the formal oxidation state of the thus obtained iodine was (III). The measured current yield was 90%.

Example 2

Electrochemical Oxidation of ICl in the Presence of a Graphite Anode

In an electrochemical cell comprising a cathodic compartment containing as the cathode a cylindrical rod of graphite having a surface area of 6 cm$^2$, and an anodic compartment containing as the anode a cylindrical rod of graphite having a surface area of 8.5 cm$^2$, where the two compartments are separated by a Fumasep® FTAM-E type anionic conduction membrane, 67.2 g of a solution of HCl 33% in water as cathodic reagent, and 124.6 g of a solution of iodine chloride having the following composition as anodic reagent:
ICl 18.9%
HCl 27.2%
H$_2$O 53.9%
were loaded.

The cell was fed with a current of 500 mA for 17 h under a voltage of about 6 volts. During electrolysis the potential of the anodic solution was detected by a Pt combined electrode (reference Ag/AgCl). The starting potential of the solution before electrolysis was found to be 680 mV, whilst at the end of the electrolysis the potential was increased to 932 mV.

Once the electrolysis reaction was completed, the anodic solution was titrated with KI in acidic conditions for the speciation of the iodine derivatives present. 1.12 meq/gram of solution of KI were consumed to obtain a point of inflection at a value of potential of 668 mV, compared to Pt combined electrode, and then 3.40 meq/gram of solution of KI were consumed to obtain a second point of inflection at a potential of 405 mV. The resulting formal oxidation state for iodine was equal to III. The measured current yield was 90%.

Example 3

Oxidation of I$_2$ to ICl by Contact with Electrochemically Oxidized Solutions of ICl To the oxidized solution of ICl, containing iodine in the formal oxidation state (III), produced according to Example 2 was added 34.3 g of solid I$_2$, operating at room temperature and keeping the mixture under stirring. The most of the solid is consumed within 390 minutes, and the residue is separated from the solution by decantation. During the dissolution of the solid iodine, the potential of the anodic solution is monitored by means of a Pt combined electrode (reference Ag/AgCl). The starting potential of the solution before the addition of I$_2$ was found to be 930 mV and once the dissolution of iodine has occurred, the potential decreased to 701 mV. The decanted solution is titrated with KI, giving a single point of inflection at a potential of 381 mV, compared to Pt combined electrode, after addition of KI (2.64 meq/gram of oxidized solution).

It was confirmed that the oxidation state of substantially all the iodine present in solution was found to be (I).

Example 4

Electrochemical Oxidation of ICl (One-Pot)

A solution of ICl in aqueous hydrochloric acid (147.2 g) containing ICl (0.284 mol) and HCl (35.99 g, 0.99 mol) is subjected to electrolysis for 23 hours as described in Example 1, feeding the cell with a current of 630 mA, and under a voltage of about 5 volts. At the end of the electrolysis, 141 g of solution containing 0.005 moles of I(I) and 0.26 moles of I (III) are discharged from the anodic compartment of the cell. The solution is then added with I$_2$ (0.27 mol), leading to 209 g of a solution containing 0.80 moles of I(I), being measured by titration. An aliquot of 69 g of this solution is then added with 68 g of a solution of HCl 33%. This solution, containing 0.26 moles of I(I), was re-subjected to electrolysis, obtaining by that 138 g of an oxidized solution containing 0.03 moles of I(I) and 0.23 mol of I(III), calculated by titration.

Example 5

Electrochemical Oxidation of ICl Using Modified Graphite Anode

In an electrochemical plate-and-frame cell made of: a cathodic compartment equipped with a compact graphite cathode, an anodic compartment equipped with a SGL Carbon specialty graphite R7510 anode, impregnated with methacrylic resin, and comprising an anion membrane type Fumasep® FTAM-E from FuMA-Tech, the following compounds were fed 1294.5 grams of 32.8% HCl solution in water as catholyte and 1301.5 grams of anolyte made of a iodine chloride solution with the following composition:
ICl 30.8%
HCl 21.1%
H2O 48.1%

The cell was fed with a current of 6.4 Amp for 20 h under a voltage of about 3.2 volt. The electrolyte flows, along the electrolysis, were 2.1 l/min for the anolyte and 0.5 l/min for catholyte. After electrolysis we titrated the anodic solution with KI, under acidic conditions, for the iodine ions speciation. The titration consumed 1:51 meq of KI for one gram of anolyte solution to give an inflection point of a potential of 697 mV compared to a combined Pt electrode, and then 4.83 meq of KI for one gram of anolyte solution to give a second inflection point of a potential of 439 mV. The resulting iodine formal oxidation state was +3. The current yield was 86%.

Example 6

Electrochemical Oxidation of ICl Using Graphite Anode

In an electrochemical plate-and-frame cell made of cathodic and anodic compartments equipped with cathode and anode made of graphite from Carbone Lorraine (high density, ultra fine grain, porosity<3% and working temperature <600° C. in oxygen) separated by an anion membrane type Fumasep FTAM-E from FuMA-Tech, the following compounds were fed: 1203.6 grams of 32.7% HCl solution in water as catholyte and 2348.8 grams of anolyte made of a iodine chloride solution with the following composition:
ICl 36.6%
HCl 8.4%
H2O 55.0%

The cell was fed with a current of 6.4 Amp for 42 h under a voltage of about 2.8 volt. The electrolyte flows along the electrolysis were 0.5 l/min for the anolyte and 0.5 l/min for catholyte. After electrolysis we titrated the anodic solution with KI, under acidic conditions, for the iodine ions speciation. The titration consumed 1.73 meq of KI for one gram of anolyte solution to give an inflection point of a potential of 659 mV compared to a combined Pt electrode, and then 5.51 meq of KI for one gram of anolyte solution to give a second inflection point of a potential of 441 mV. The resulting iodine formal oxidation state was +3. The current yield was 91%.

Example 7

Electrochemical Oxidation of ICl Using Glassy Carbon Anode

In an electrochemical plate-and-frame cell made of cathodic and anodic compartments equipped with cathode and anode made of glassy carbon Sigradur® from HTW Gmbh and separated by an anion membrane type Neosepta AHA from Tokuyama, the following compounds were fed 1888.0 grams of 33.0% HCl solution in water as catholyte and 1885.0 grams of anolyte made of a iodine chloride solution with the following composition:
ICl 31.4%
HCl 21.8%
H2O 46.8%

The cell was fed with a current of 10.0 Amp for 18 h under a voltage of about 6.5 volt. The electrolyte flows along the electrolysis were 5.0 l/min for the anolyte and 0.5 l/min for catholyte. After electrolysis we titrated the anodic solution with KI, under acidic conditions, for the iodine ions speciation. The titration consumed 1.59 meq of KI for one gram of anolyte solution to give an inflection point of a potential of 711 mV compared to a combined Pt electrode, and then 5.07 meq of KI for one gram of anolyte solution to give a second inflection point of a potential of 440 mV. The resulting iodine formal oxidation state was +3. The current yield was 91%.

The invention claimed is:

1. A process for the electrochemical preparation of ICl comprising the steps of:
   a. electrochemically oxidizing 1 mole of starting ICl in acidic aqueous solution, to give $ICl_3$ wherein iodine has an oxidation state equal to (III);
   b. reacting said $ICl_3$ with iodine; and
   c. obtaining 3 moles of ICl.

2. The process according to claim 1, wherein said electrochemical oxidation is carried out in an electrolytic cell wherein the anodic and cathodic compartments are separated by a ion permeable membrane.

3. The process according to claim 2, wherein the membrane is selectively permeable to anions or cations.

4. The process according to claim 2, wherein the electrode of the cathodic compartment is made of graphite.

5. The process according to claim 2, wherein the electrode of the anodic compartment is made of: platinum, graphite, modified graphite or glassy carbon.

6. The process according to claim 1, in the presence of a cathode solvent system comprising: a strong acid mixed with water, a $C_1$-$C_4$ alcohol or mixture thereof.

7. The process according to claim 6, wherein said strong acid is hydrochloric acid or sulphuric acid.

8. The process according to claim 6, wherein said cathode solvent system comprises a mixture of water and hydrochloric acid.

9. The process according to claim 8, wherein said hydrochloric acid has a concentration comprised from 5% to 40% by weight.

10. The process according to claim 1, wherein the starting ICl in the acidic aqueous solution has a concentration comprised from 15% to 40% by weight.

11. The process according to claim 1, wherein a part of the produced ICl is re-introduced as a starting reagent in the anodic compartment.

12. The process according claim 1, wherein the electrochemical oxidation is carried out in galvanostatic or potentiostatic mode, operating at values of current density comprised from 50 to 150 $mA/cm^{-2}$.

13. The process according to claim 1, comprising transferring the solution obtained in step-a into a separate reactor, before carrying out the next step-b.

14. The process according to any one of claim 1, 5, 6 or 11 further comprising iodinating a compound of formula (I)

I wherein:
R is —N(R')$_2$ or —OH;
R1 is independently in each occurrence —COOR', —CON(R')$_2$; and
R' is independently in each occurrence hydrogen or (C1-C4) linear or branched alkyl optionally substituted by one or more hydroxy groups present as such or in a protected form, to obtain a compound of formula (II)

II

15. The process according to claim 14 wherein:
R is a hydroxy —OH or amino group —NH$_2$ and the groups R1 are the same and are selected from the group consisting of —COOH and —CONHR', wherein R' is selected from the group consisting of —CH(CH$_2$OH)$_2$ and —CH$_2$(CHOH)CH$_2$OH.

16. The process according to claim 5, in the presence of a cathode solvent system comprising: a strong acid mixed with water, a $C_1$-$C_4$ alcohol or mixture thereof.

17. The process according to claim 10, wherein a part of the produced ICl is re-introduced as a starting reagent in the anodic compartment.

* * * * *